(12) United States Patent
Truckai et al.

(10) Patent No.: US 12,029,445 B2
(45) Date of Patent: Jul. 9, 2024

(54) SURGICAL INSTRUMENT AND METHOD OF USE

(71) Applicant: Meditrina, Inc., San Jose, CA (US)

(72) Inventors: Tamas J. Truckai, Saratoga, CA (US); Csaba Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 781 days.

(21) Appl. No.: 17/074,347

(22) Filed: Oct. 19, 2020

(65) Prior Publication Data

US 2021/0128188 A1 May 6, 2021

Related U.S. Application Data

(60) Provisional application No. 62/923,288, filed on Oct. 18, 2019.

(51) Int. Cl.
*A61B 17/32* (2006.01)

(52) U.S. Cl.
CPC ............ *A61B 17/32002* (2013.01); *A61B 2017/320024* (2013.01); *A61B 2017/320032* (2013.01)

(58) Field of Classification Search
CPC .. A61B 17/32002; A61B 2017/320024; A61B 2017/320032; A61B 2017/32006; A61B 17/142; A61B 17/144; A61B 17/3201
See application file for complete search history.

(56) References Cited

U.S. PATENT DOCUMENTS

| | | | |
|---|---|---|---|
| 4,815,642 A | | 3/1989 | Ray |
| 5,423,845 A | * | 6/1995 | McDaniel ............ A61B 17/142 606/178 |
| 6,342,061 B1 | | 1/2002 | Kauker et al. |
| 8,313,502 B2 | | 11/2012 | Heisler |
| 9,839,441 B2 | * | 12/2017 | Hayes .............. A61B 17/32002 |
| 2006/0196038 A1 | * | 9/2006 | Van Wyk ......... A61B 17/32002 29/557 |
| 2008/0021488 A1 | | 1/2008 | Berberich |
| 2008/0243153 A1 | | 10/2008 | Nguyen et al. |
| 2012/0239064 A1 | | 9/2012 | Cartier et al. |
| 2013/0274751 A1 | | 10/2013 | Steinwachs et al. |
| 2013/0331833 A1 | | 12/2013 | Bloom |
| 2014/0277040 A1 | | 9/2014 | Hayes et al. |
| 2015/0209080 A1 | | 7/2015 | Sullivan et al. |
| 2016/0346036 A1 | | 12/2016 | Orczy-Timko et al. |
| 2017/0056047 A1 | | 3/2017 | Keller et al. |
| 2019/0021765 A1 | | 1/2019 | Magno et al. |
| 2019/0290327 A1 | | 9/2019 | Magno et al. |
| 2019/0298403 A1 | | 10/2019 | Willhite et al. |
| 2019/0321095 A1 | | 10/2019 | Germain et al. |
| 2019/0374246 A1 | * | 12/2019 | Malkevich ......... A61B 18/1485 |
| 2020/0146703 A1 | | 5/2020 | Truckai et al. |
| 2021/0007793 A1 | | 1/2021 | Germain et al. |
| 2021/0282799 A1 | | 1/2021 | Germain et al. |
| 2022/0047294 A1 | | 2/2022 | Truckai et al. |
| 2022/0323073 A1 | | 10/2022 | Gurtner et al. |
| 2022/0387060 A1 | | 12/2022 | Truckai et al. |

FOREIGN PATENT DOCUMENTS

EP 1698290 11/2009

* cited by examiner

*Primary Examiner* — Sarah A Long
(74) *Attorney, Agent, or Firm* — Levine Bagade Han LLP

(57) ABSTRACT

Instruments and methods for resecting tissue from the interior of a patient's body with a motor-driven rotating tubular cutter.

21 Claims, 12 Drawing Sheets

SURGICAL INSTRUMENT AND METHOD OF USE

RELATED APPLICATION INFORMATION

This application claims benefit of U.S. provisional application 62/923,288 filed on Oct. 18, 2019, the entirety of which is incorporated by reference.

BACKGROUND OF THE INVENTION

Field of the Invention

The present disclosure relates to an instrument and method for resecting tissue from the interior of a patient's body with a motor-driven rotating tubular cutter.

SUMMARY

Some aspects in accordance with principles of the present disclosure relate to a tissue-resecting device for use with a powered surgical tool. The resection device or instrument includes an outer sleeve assembly and a co-axial inner sleeve assembly. The outer sleeve comprises a tubular member extending distally to a typically rounded distal end, with a cutting window in the distal region thereof. The window may have a sharp beveled edge but more often has window edges with a plurality of sharp teeth for engaging and gripping tissue. The inner sleeve also has a cutting tip which includes a windowed cutting edge configured with exceptionally sharp teeth that are adapted to perform two functions. First, a needle-like tip of each tooth is configured to pierce and grip tissue and a second lower blade edge of each tooth is adapted to shear the tissue captured by the needle-like tip portions as the inner window passes the cutting edges of the outer sleeve window.

Other aspects in accordance with the present invention relate to features of the outer sleeve in its distal cutting window which will be described further below.

The present disclosure includes surgical instruments for resecting tissue. For example, one variation of such an instrument includes an elongated shaft extending about a longitudinal axis comprising co-axial outer and inner sleeves having cooperating respective outer and inner cutting windows in distal ends thereof; wherein the inner cutting window has circumferentially spaced-apart first and second cutting edges each with teeth therein and wherein the teeth, when viewed in a direction parallel to the axis, define a base portion extending radially to a lateral portion and thereafter radially to a needle-like tip portion configured for penetrating tissue; wherein the needle-like tip portion, when viewed in cross-section from a direction parallel to the axis defines a first acute angle and wherein the needle-like tip portion, when viewed in cross-section from a direction transverse to the axis, also defines a second acute angle. In one example, the first acute angle can be less than 44 degrees. In another variation, the second acute angle can be less than 44 degrees, less than 42 degrees, or less than 40 degrees.

In another variation of the device a height of the needle-like tip portion from the tip to the lateral portion is at least 0.010". In another variation of the device the needle-like tip portion when viewed in cross-section from a direction transverse to the axis defines a hollow ground cutting edge. In another variation of the device the height of the teeth from said tip to the base of the base portion is at least 0.025". In another variation of the device the lateral portion is configured with a lateral cutting edge extending an axial direction at least 0.005". In another variation of the device lateral cutting edges are provides on both sides of the needle-like tip portion. In another variation of the device the lateral cutting edges when viewed in cross-section from a direction transverse to the axis define an acute angle of less than 44 degrees, less than 42 degrees, or less than 40 degrees.

In another variation of the device the lateral cutting edges when viewed in cross-section from a direction transverse to the axis define a hollow ground cutting edge. In another variation of the device, the device further comprises base cutting edges that are intermediate adjacent lateral portions that extend an axial direction of at least 0.020".

In another variation of the device, the device further comprises base cutting edges that when viewed in cross-section from a direction transverse to the axis define an acute angle of less than 44 degrees, less than 42 degrees, or less than 40 degrees. In another variation, the device can include base cutting edges that when viewed in cross-section from a direction transverse to the axis define a hollow ground cutting edge.

In another variation of the device the tip of needle-like tip portion is at an outer periphery of the inner sleeve wall when viewed in cross-section from a direction transverse to the axis.

In another variation of the device, the lateral cutting edge and the base cutting edge are at an outer periphery of the inner sleeve wall around the inner window when viewed in cross-section from a direction transverse to the axis. In another variation of the device the outer cutting window has circumferentially spaced-apart first and second beveled cutting edges. In another variation of the device the outer cutting edges are at an inner periphery of the inner sleeve wall around the outer window when viewed in cross-section from a direction transverse to the axis. In another variation, of the device the outer cutting window has circumferentially spaced-apart first and second cutting edges each with outer teeth therein. In another variation, the device can include the tip of the outer teeth that are at an inner periphery of the inner sleeve wall around the outer window when viewed in cross-section from a direction transverse to the axis.

The present disclosure also includes surgical instruments for resecting tissue, comprising: an elongate tubular cutting member extending about a longitudinal axis to a distal end having a cutting window communicating with an interior channel therein; and the cutting window having circumferentially spaced-apart first and second cutting edges each with teeth therein; wherein the cutting edges include at least first and second edge portions with differing edge angles; and wherein each such edge angle, when viewed in cross-section from a direction transverse to the axis, defines an acute angle. For example, the acute angle can be less than 44 degrees.

Another variation of a surgical instrument for resecting tissue includes an elongate tubular cutting member extending about a longitudinal axis to a distal end having a cutting window communicating with an interior channel therein; the cutting window having circumferentially spaced-apart first and second cutting edges each with teeth therein; wherein the teeth, when viewed in a direction parallel to the axis, define a base portion extending to a shoulder portion and thereafter to a needle-like tip portion; and wherein the needle-like tip portion, when viewed in cross-section from a direction transverse to the axis, defines an acute angle of less than 44 degrees, less than 42 degrees, or less than 40 degrees.

Another surgical instrument for resecting tissue include an elongate tubular cutting member extending about a longitudinal axis to a distal end having a cutting window communicating with an interior channel therein; the cutting window having circumferentially spaced-apart first and second cutting edges each with teeth therein; wherein the teeth, when viewed in a direction parallel to the axis, define a base portion extending to a shoulder portion and thereafter to a needle-like tip portion; and wherein the tip portion has a height dimension that extends over a radial angle ranging from 10 degrees to 25 degrees; and wherein the tip portion, when viewed in cross-section from a direction transverse to the axis, defines an acute angle of less than 44 degrees, less than 42 degrees, or less than 40 degrees Another surgical instrument for resecting tissue includes an elongate tubular cutting member extending about a longitudinal axis to a distal end having a cutting window communicating with an interior channel therein; the cutting window having circumferentially spaced-apart first and second cutting edges each with teeth therein; wherein the teeth, when viewed in a direction parallel to the axis, define a base portion extending to a shoulder portion and thereafter to a needle-like tip portion; wherein the tip portion has a height dimension that extends over a radial angle ranging from 10 degrees to 25 degrees; and wherein the shoulder portion has a height dimension that extends over a radial angle ranging from 10 degrees to 25 degrees.

BRIEF DESCRIPTION OF THE DRAWINGS

FIGS. 10A-10D are schematic cross-sectional views of the working end of FIGS. 1-8 in a method of use wherein the teeth perform the two functions of first piercing and gripping hard tissue and then shearing off a tissue chip for aspiration away from the treatment site, wherein FIG. 10A shows the needle-like tip rotating toward hard tissue engaged by the windows.

FIG. 10B shows further rotation of the inner sleeve following the position of FIG. 10A where the needle-like tip pierces into the hard tissue.

FIG. 10C shows further rotation of the inner sleeve following the position of FIG. 10B where the needle-like tip continues to pierce and grip the hard tissue with the shoulder cutting edges approaching the outer sleeve window edges.

FIG. 10D shows further rotation of the inner sleeve where the shoulder cutting edges pass the outer sleeve window edges to thereby shear off a tissue chip.

DETAILED DESCRIPTION

Surgical probes of the present disclosure may be utilized in various types of surgeries, including but not limited to gynecology procedures such a myomectomies and polypectomies, ENT procedures, arthroscopies, spine surgeries, tumor resection procedures and the like.

Figure 1:
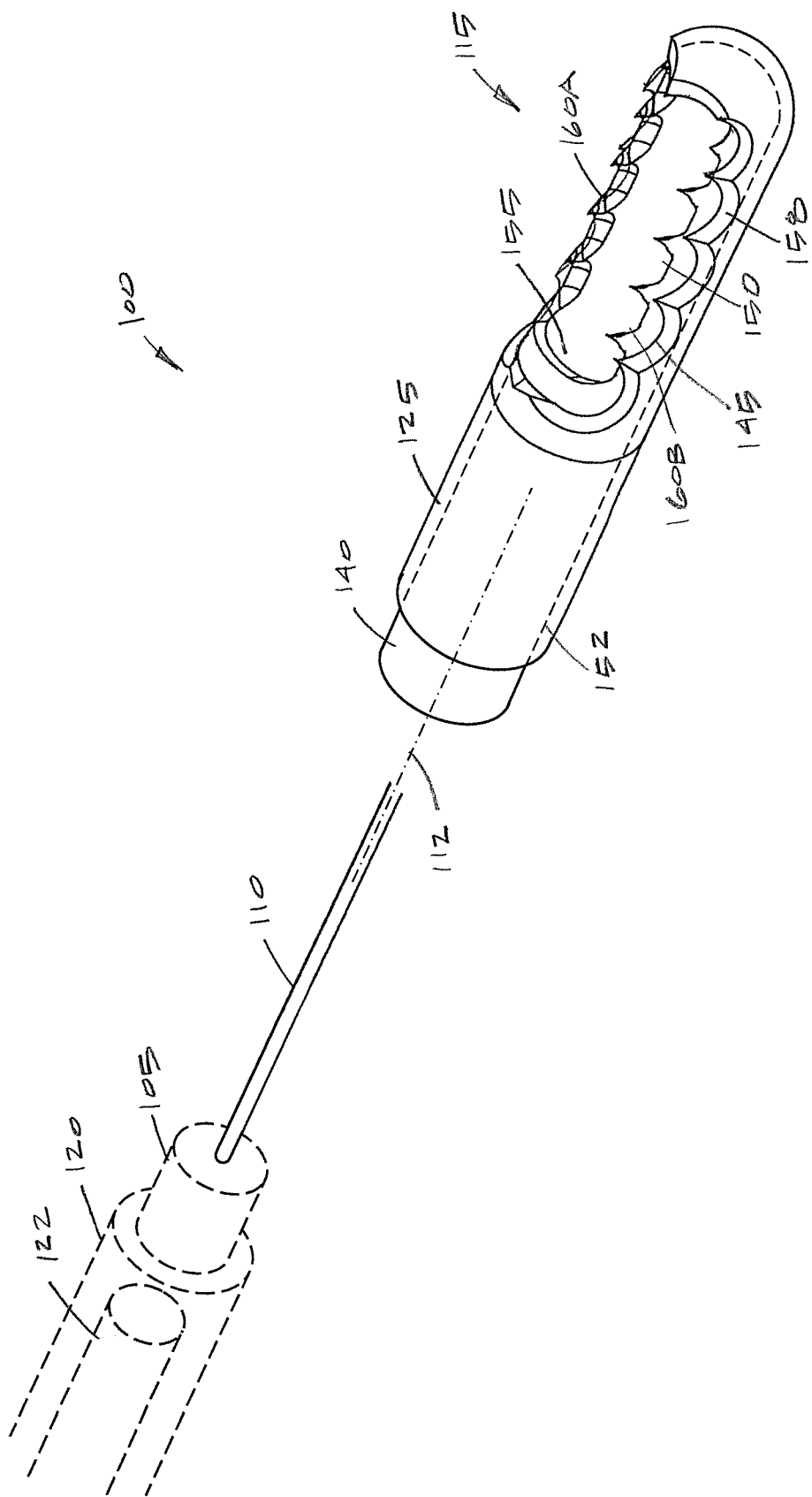
FIG. 1 is a perspective view of a surgical cutting device or resecting probe corresponding to the invention that is adapted for resecting and removing tissue from a patient's body, wherein and elongate shaft portion of the probe includes a windowed outer sleeve and a rotatable windowed inner sleeve with sharp teeth for sequentially piercing and then shearing tissue when rotated or rotationally oscillated.

A surgical cutting probe 100 in accordance with aspects of the present invention is shown in FIG. 1. The cutting probe 100 includes a proximal hub 105 coupled to an elongate shaft 110 extending about longitudinal axis 112 to a distal working end 115. The hub 105 can be detachably coupled to a handpiece 120 that carries a motor drive 122 (phantom view) as is known in the art.

The probe 100 and its shaft 110 include co-axial outer and inner sleeves 125 and 140, respectively, wherein the inner sleeve 140 is rotatable by the motor drive 122. The inner sleeve 140 includes a proximal inner hub member (not shown) that rotates within the proximal hub 105 as is known in the art. The outer sleeve 125 has a distal cutting window 145 therein. The inner sleeve 140 has a cooperating distal inner cutting window 150 which rotates within the bore 152 of the outer sleeve 125.

The handpiece 120 thus is adapted for driving the rotational movement of the inner sleeve 125 and the inner cutting window 150. The handpiece 120 also is configured with an aspiration channel that couples to the aspiration passageway or bore 155 in the inner sleeve 140 for extracting fluids and tissue chips from a resection site in a patient's body. Thus, the inner cutting window 150 of inner sleeve 140 functions as a fluid outflow port communicating with the inner sleeve bore 155 that is coupled through tubing (not shown) to a remote negative pressure source.

Optionally, a fluid inflow path can be provided to the proximal hub 105 of the probe 100 to deliver fluid to the space between the inner and outer sleeves, 125 and 140, so that the outer sleeve window 145 of the outer sleeve 125 functions as a fluid inflow port. Such a fluid inflow path, in turn, would be is adapted for connection to inflow tubing (not shown) that is coupled to a pressurized fluid source.

Figure 2A:
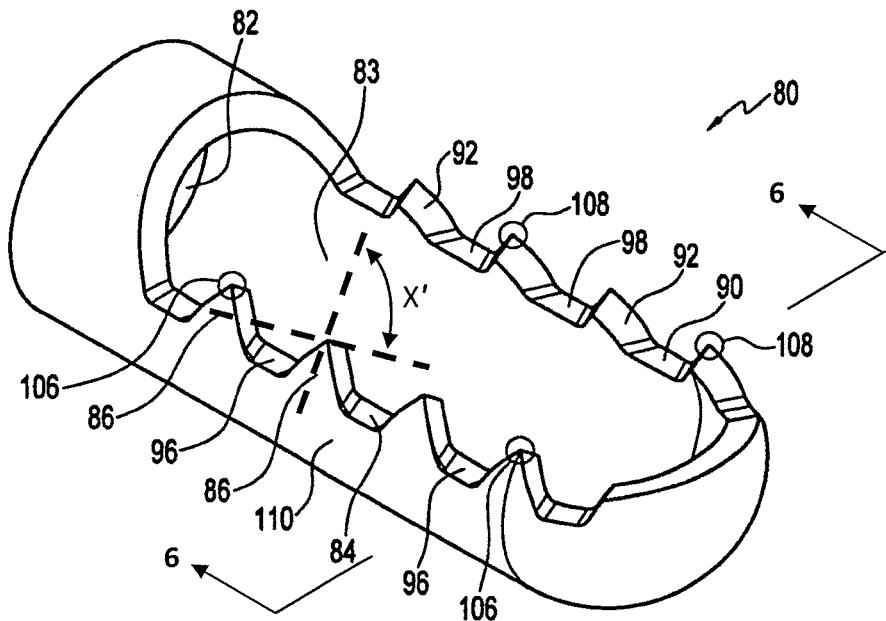
FIG. 2A is a perspective view of a prior art inner sleeve cutting window of a tubular cutter which illustrates typical cutting-edge teeth that cannot pierce into hard tissues 5th.
Figure 2B:
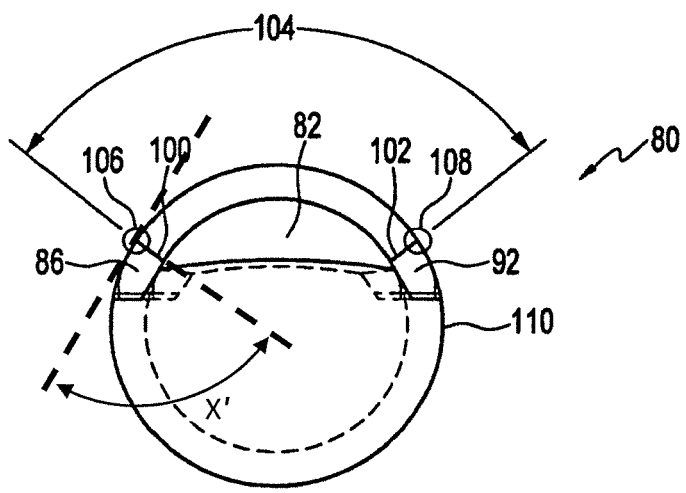
FIG. 2B is a cross-sectional view of the cutting member of FIG. 2A taken along line 2B-2B of FIG. 2A.
Figure 3:
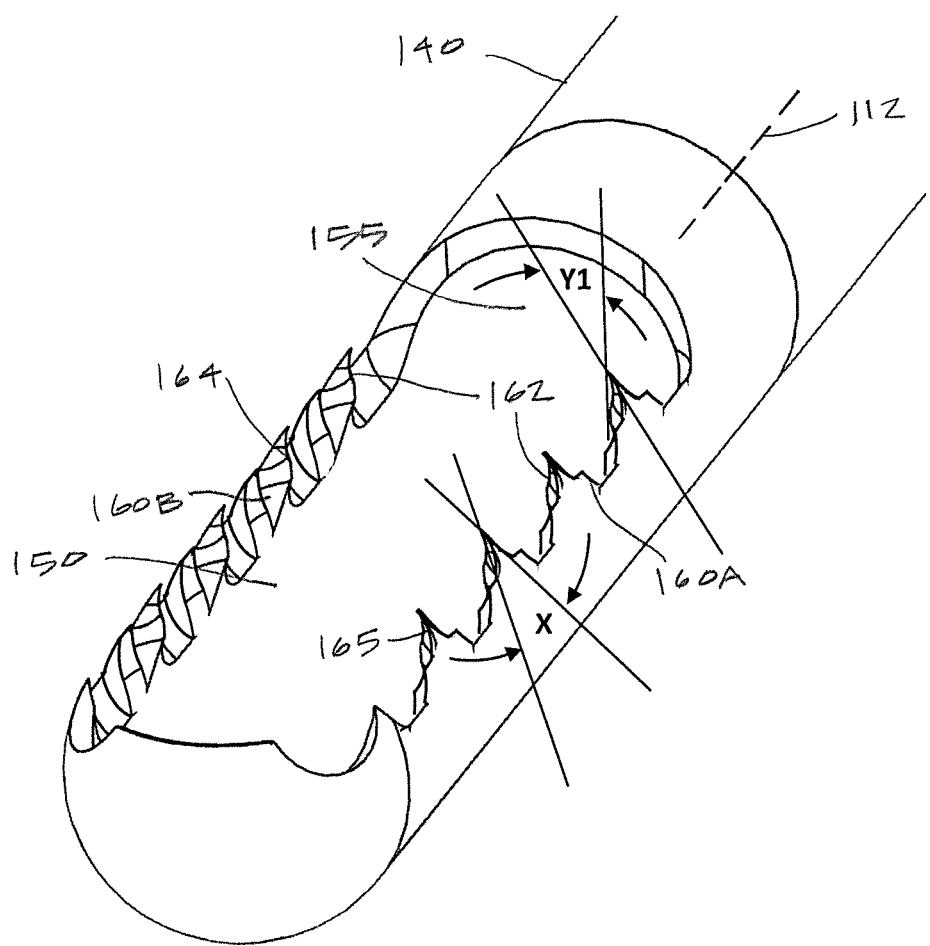
FIG. 3 is a perspective view of the cutting edges of the inner sleeve window corresponding the invention wherein the teeth have a first functional portion consisting of a very sharp needle-like tip for penetrating tissue and shoulder or lateral portions that extend axially relative to the axis of the of probe.

After understanding the general principles of the probe 100, several particular features of the working end of the invention are shown in greater detail in FIGS. 3, in 4 and 5, which can be compared to prior art working end shown in FIGS. 2A and 2B. The prior art illustrations of FIGS. 2A and 2B are reproductions of FIGS. 19 and 20 from European Patent Specification EP1698290B1 filed Feb. 3, 2006 by Van Wyk, also published US Patent Application 20060196038.

In FIG. 3, the distal end 156 of inner sleeve 140 is shown separated from the outer sleeve 125. In general terms, the inner sleeve 140 is rotatably disposed within the bore 152 in the outer sleeve 125 such that the inner sleeve cutting window 150 rotates to cut or shear tissue captured against the cutting edges 158 of the outer sleeve cutting window 145 (see FIG. 1).

As it can be seen in FIG. 3, the inner sleeve cutting window 150 has circumferentially spaced-apart first and second cutting edges 160A and 160B with a plurality of teeth 162 in each cutting edge with cutting faces 164 beveled inwardly. A key aspect of the invention relates to the shape of the teeth 162 which are configured with elements for performing two different functions. First, the teeth 162 include very sharp needle-like tip portions 165 for piercing and gripping hard tissue during rotation. Second, the teeth 162 include sharp lateral edges 170a and 170b that function as tissue-shearing elements to cut and shear tissue that is engaged and gripped by the teeth as the inner sleeve window 150 rotates towards a cooperating opposing cutting edge 158 of the outer sleeve cutting window 145 during use. With the In FIGS. 3, 4 and 5, it can be seen that the teeth 162, when viewed in a direction parallel to the axis 112, define a base portion 172 extending radially to the shoulder or lateral portions 170a and 170b and thereafter radially to a needle-like tip portion 165 with vertex 180 configured for piercing and gripping tissue, but not for shearing off tissue chips.

Figure 5:
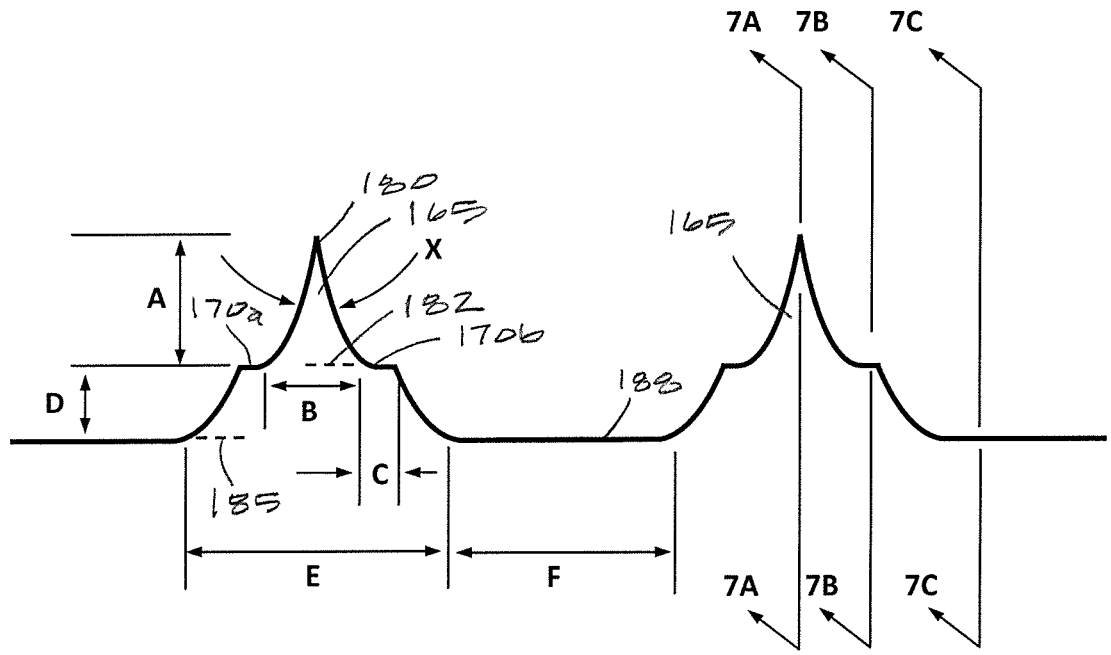
FIG. 5 is an enlarged schematic view of the teeth of FIG. 4 showing the dimensions of various aspects of the teeth and the cutting edges.
Figure 4:
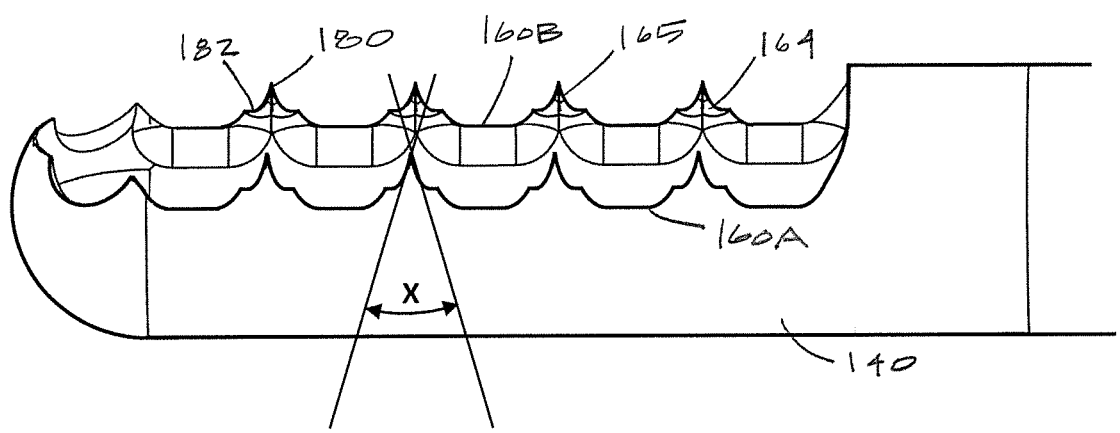
FIG. 4 is a side elevation view of the distal portion of the inner sleeve of FIG. 3 showing the inner cutting window.

Referring to FIGS. 4 and 5, the needle-like tip portions 165 of the teeth 162, when viewed in a direction parallel to the axis 112, extend upwardly at a sharp angle so that the tip or vertex 180 is exceptionally sharp for piercing and penetrating tissue. In one variation, the included angle X of the tip portion 165 defines an acute angle of less than 44 degrees, less than 42 degrees, or less than 40 degrees, as best shown in FIGS. 4 and 5. The height A of the teeth 162 from its tip or the vertex 180 to the tip base 182 is at least 0.015" and often greater than 0.020". The axial dimension B of the tip base 182 is between 0.015" and 0.040". Stated another way, referring to FIG. 6, the height A of a needle-like tip portion 165 can be defined by its radial angle RA1 which ranges from 15° to 20° or more (see FIG. 6). In one variation shown in FIG. 6, the outer diameter D1 is 0.133" and the inner diameter D2 is 0.110" with a wall thickness W of 0.012" (not limiting).

Figure 7A:
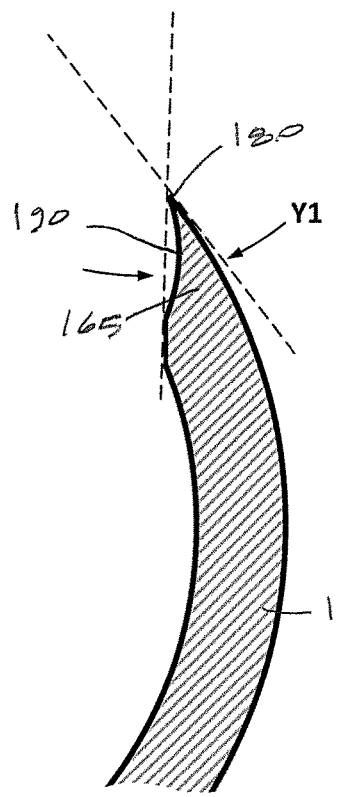
FIG. 7A is an enlarged cross-sectional view of the tooth of FIG. 5 taken along line 7A-7A of FIG. 5 showing the surface angles of the needle-like tip portion, which is defined by a tangent at the outer surface of the tooth vertex and a plane extending across an inner face of the tooth.

FIG. 7A shows the needle-like tip portion 165 of a tooth 162 from a different direction showing its sharpness. In FIG. 7A, it can be seen that the needle tip portion 165, when viewed in cross-section from a direction transverse to the axis 112, defines an acute angle Y1 of less than 44 degrees, less than 42 degrees, or less than 40 degrees.

In contrast, typical prior art teeth 92 of an inner sleeve working end 80 of a tubular cutter are shown in FIGS. 2A and 2B where the teeth are not sharp enough to pierce into tissue. As can be seen in FIGS. 2A and 2B, the included angle X' of the tip 106 of the such teeth is 92 close to 90°.

Figure 6:
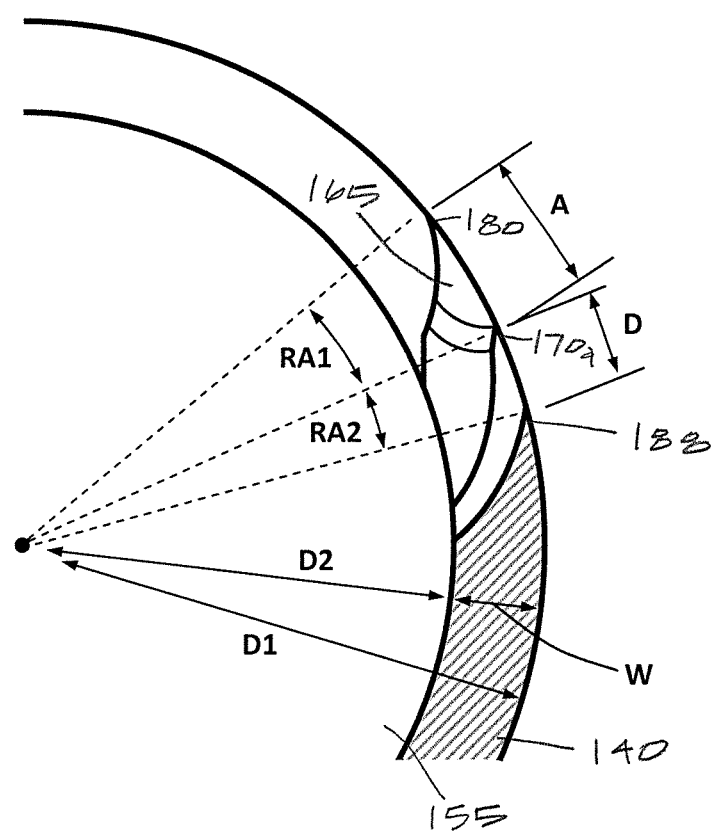
FIG. 6 is a sectional view of the cutting member of FIG. 4 taken along line 6-6 of FIG. 4 showing the radial angle over which the needle-like teeth extend as well as the radial angle of other elements of the cutting edge.
Figure 7B:
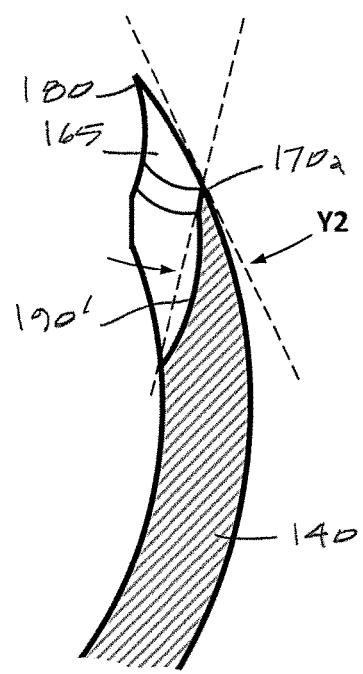
FIG. 7B is similar to that of FIG. 7A but showing a cross-sectional view of the cutting edge of the lateral portion of the cutting edge and tooth of FIG. 5 taken along line 7B-7B of FIG. 5

Referring again to FIGS. 4 and 5, the shoulder or lateral portions 170a, 170b of teeth 162 are also very sharp. In one variation, as shown in FIG. 7B, the acute angle Y2 of the cutting edge of a tooth lateral portion is less than 44 degrees, less than 42 degrees, or less than 40 degrees. Referring back to FIG. 5, the lateral portions 170a, 170b have cutting edges that extend in an axial direction and have a dimension C of at least 0.005" on either or both sides of the needle-like tip portion 165. In some variations, the generally axial dimension C is between 0.010" and 0.040". In one variation, the height D of a tooth from the lateral portions 170a, 170b to the base 185 of the tooth 162 is typically greater than 0.05" and often greater than 0.010" (see FIG. 5). Stated another way, referring to FIG. 6, the height D of a tooth 162 from the base 185 to the lateral portions 170, 170b can be defined by its radial angle RA2 which ranges from 15° to 25 degrees. The axial dimension E of the base 185 of the teeth is between 0.010" and 0.040".

Figure 7C:
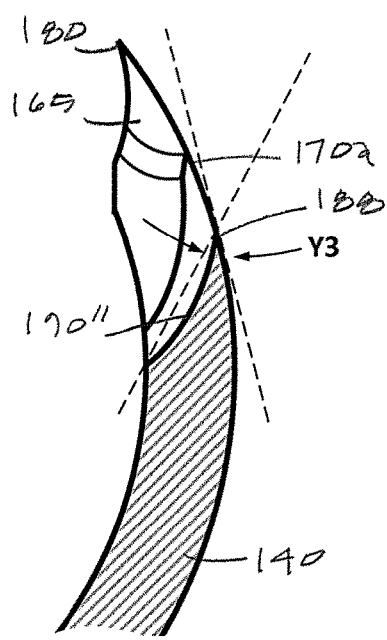
FIG. 7C is similar to that of FIGS. 7A-7B but showing a cross-sectional view of the sharp edge of the base cutting edge that extends between the teeth of the cutting edge of the inner sleeve window taken along line 7C-7C of FIG. 5

Still referring to FIGS. 4 and 5, the cutting edges 160A, 160B of window 150 are also configured with a base cutting edge 188 that extends axially between the shoulder or lateral portions 170a, 170b of the teeth 162. The base cutting edges are also very sharp, and in one variation have an acute angle Y3 of less than 44 degrees, less than 42 degrees, or less than 40 degrees as can be seen in FIGS. 6 and 7C. The base cutting edge 188 extends in an axial direction a dimension F which can range from 0.020"

In some variations, as can be seen in FIGS. 6, 7A, 7B, and 7C, the sharp edges of needle-like tip portion 165, the lateral portions 170a, 170b and the base portion 185 have hollow ground faces 190, 190' and 190' which enhance the sharpness of such edges for tissue gripping and for the enhancing the cutting ability of such edges (see FIGS. 7A-7C). In some variations, such hollow ground faces of the cutting edges can be machined with a ball-end mill to provide a selected radius of the hollow ground edge. In other variations, the machining process can use an end-mill that creates a parabolic hollow ground shape in the face of the cutting edges.

Figure 8:
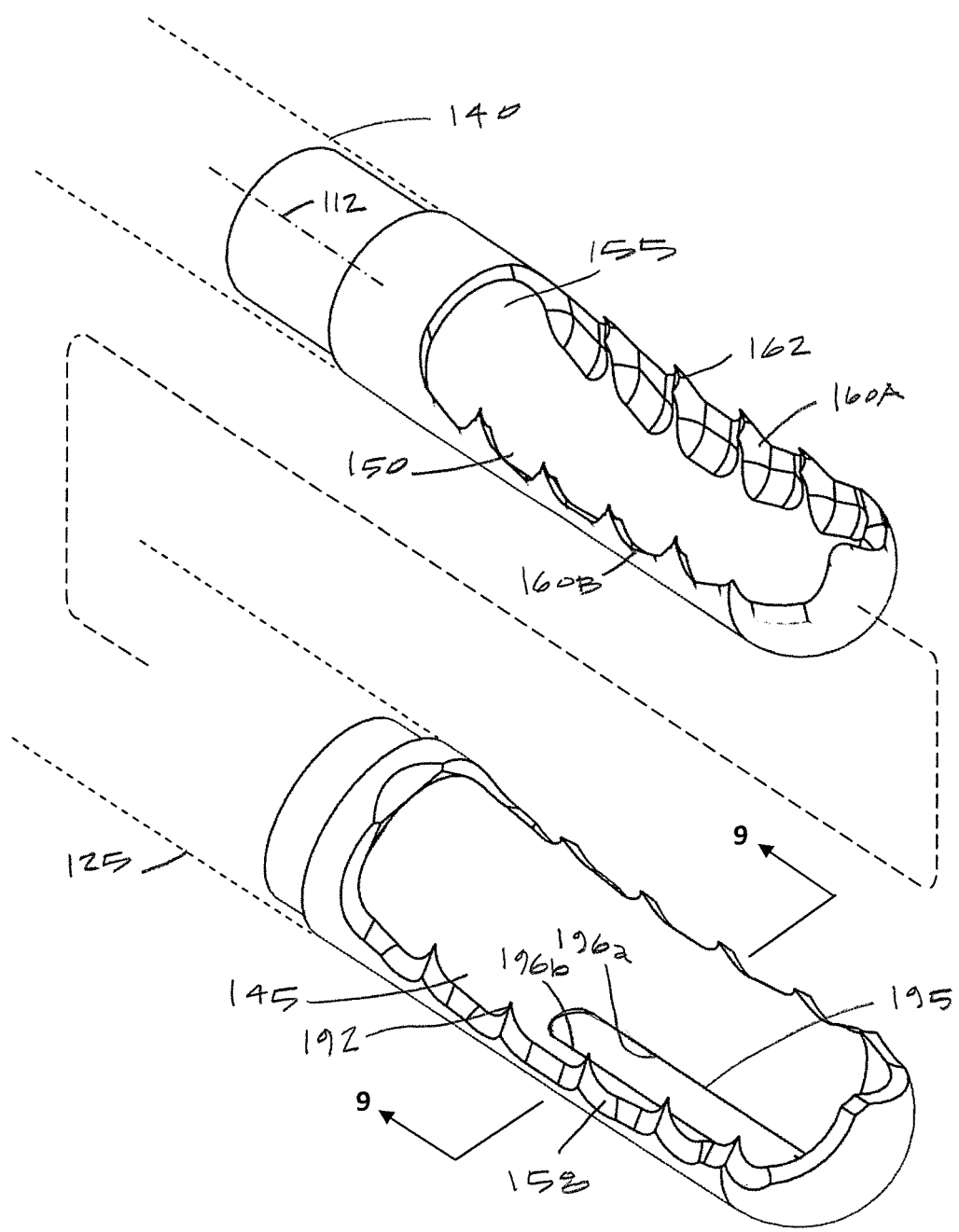
FIG. 8 is an exploded view of the distal ends of both as inner sleeve and an outer sleeve showing the teeth and features of the cutting edge of the outer sleeve window together with a secondary window in the outer sleeve opposing the primary cutting window.

Now turning to FIG. 8, the distal ends of an outer sleeve 125 and inner sleeve 140 are shown in an exploded view to illustrate the configuration of teeth 192 on the cutting edges 158 of the outer sleeve cutting window 145. In FIG. 8, the outer sleeve 125 has teeth 192 that are aligned with teeth 162 of the inner sleeve window 150 which has been found to be effective for engaging and shearing tissue. The teeth 192 in the outer cutting edge 158 of the outer window 145 again have very sharp angles that are beveled outwardly with such angles being less than 50° and often less than 45°.

As also can be seen in FIG. 8, one variation of the outer sleeve 125 includes a secondary window 195 in the distal end of the sleeve opposing the primary cutting window 145. In general, such a secondary window 195 is useful for maintaining fluid flows through the probe during use since at least a portion of either window 145 or 195 will be open to the window 150 and aspiration passageway or bore 155 of the inner sleeve 140.

Figure 9:
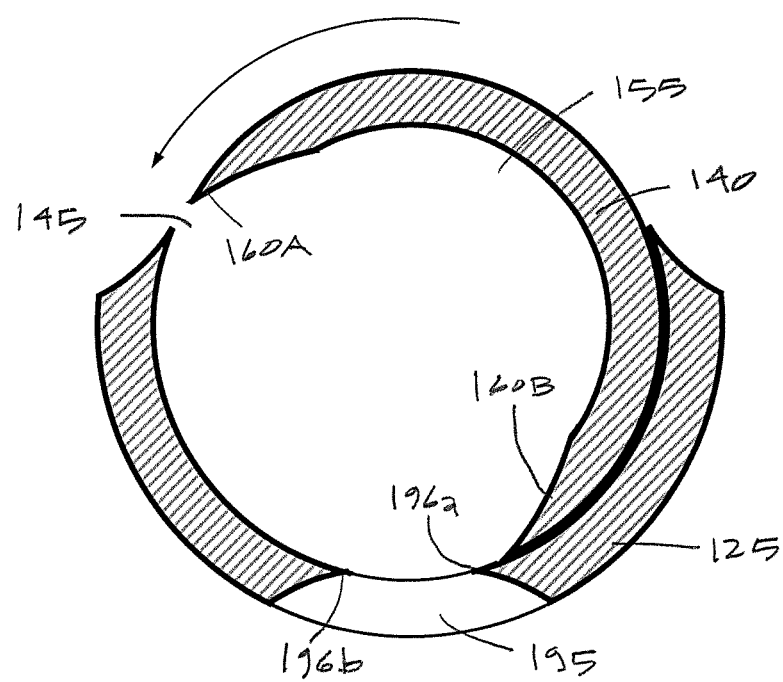
FIG. 9 is a cross-sectional view of the outer sleeve window and secondary window of FIG. 8 taken along line 9-9 of FIG. 8 and further showing the rotation of the inner sleeve.

In one variation, as shown in FIGS. 8 and 9, the secondary window 195 can be configured with lateral, sharp cutting edges 196*a* and 196*b* for engaging and shearing tissue when cooperating with the rotating inner sleeve 140 and cutting edges 160A and 160B. In other words, if the physician wishes to resect tissue less aggressively than is possible with the primary cutting window 145 cooperating with the rotating inner sleeve 125, the physician may engage the targeted tissue in the secondary window 195 and rotate the inner sleeve 140 which will resect far smaller amounts of tissue in a very precise manner. FIG. 9 shows a cross-sectional view of the secondary cutting window 195 with sharp edges 196*a* and 196*b*. The sharp edges 196*a* and 196*b* of the secondary window 195 also may be serrated or otherwise configured with teeth similar to those described previously.

Figure 10A:
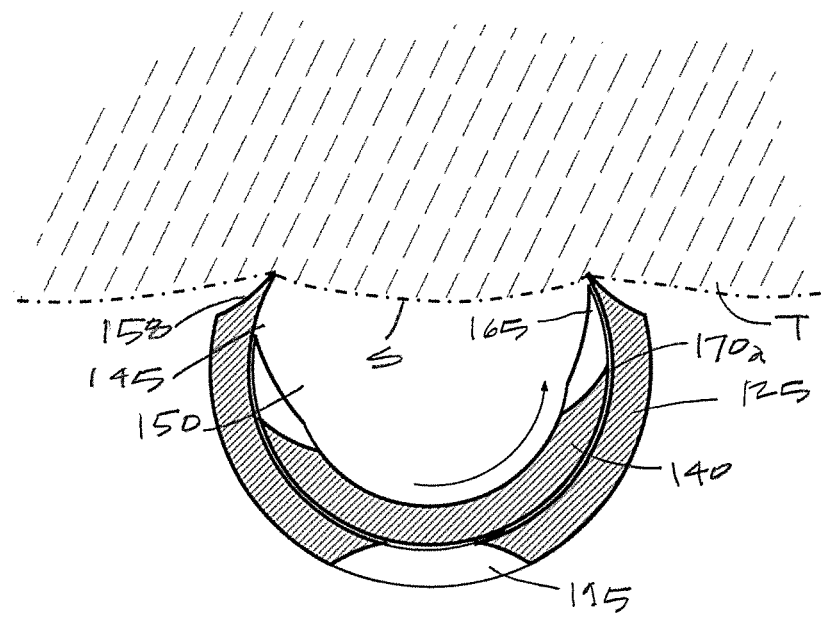
Figure 10B:
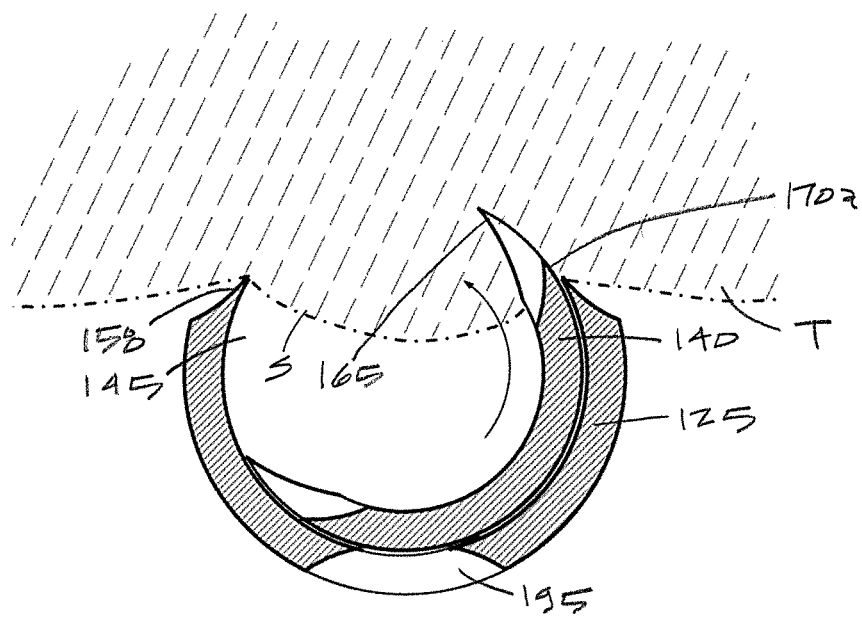
Figure 10C:
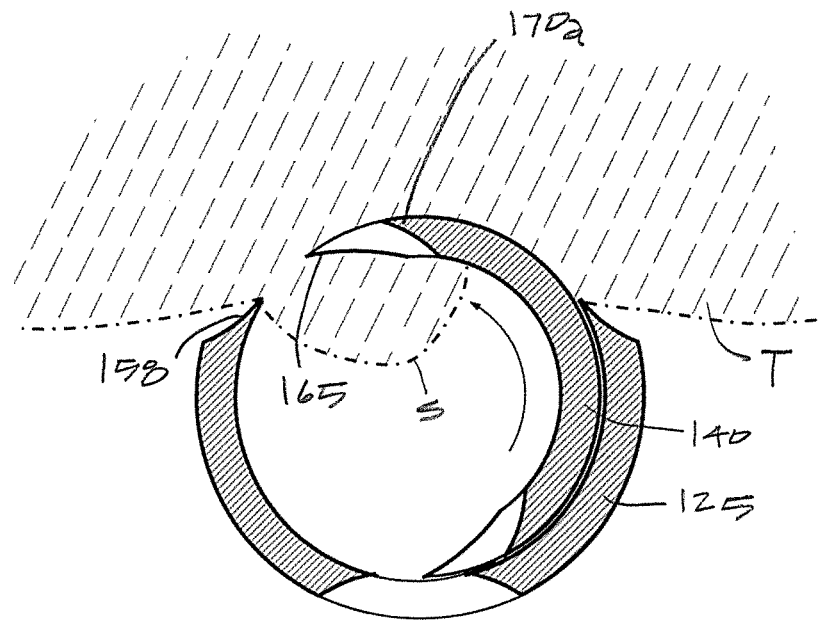
Figure 10D:
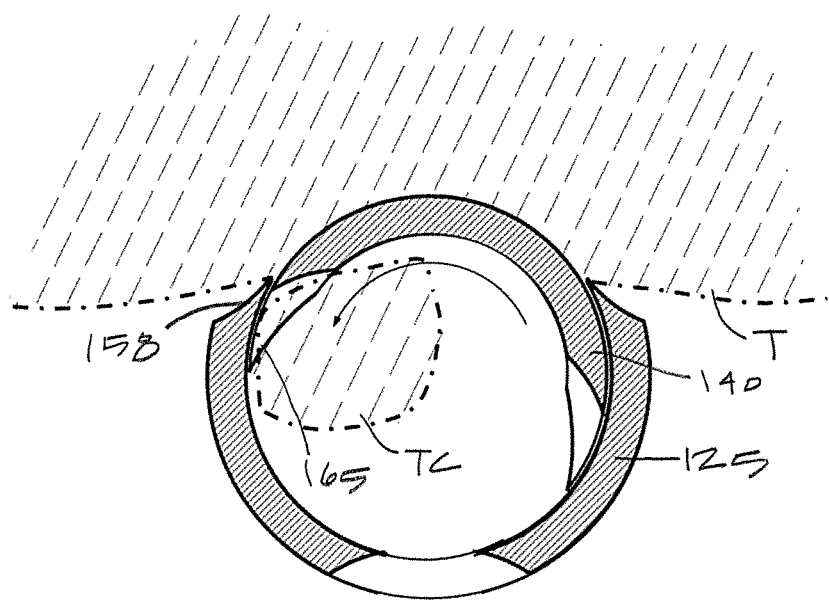
Figure 11A:
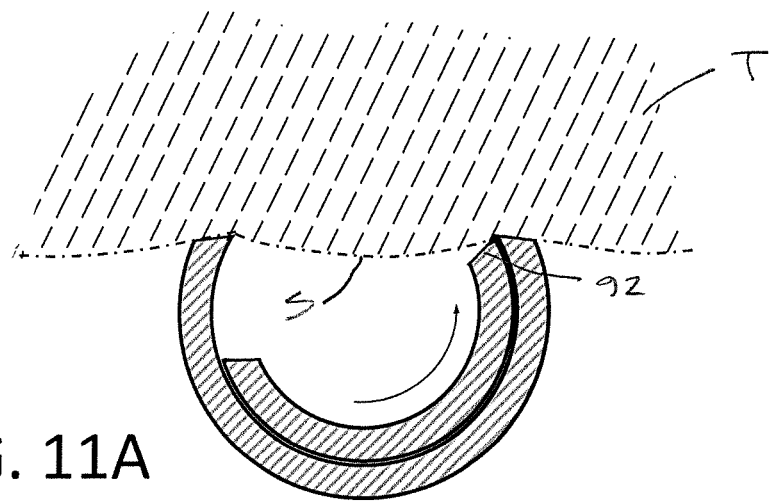
FIGS. 11A-11B are cross-sectional views similar to those of FIGS. 10A-10B but showing the exemplary prior cutter of FIGS. 2A-2B without exceptionally sharp needle-like teeth is ineffective at resecting hard tissue.
Figure 11B:
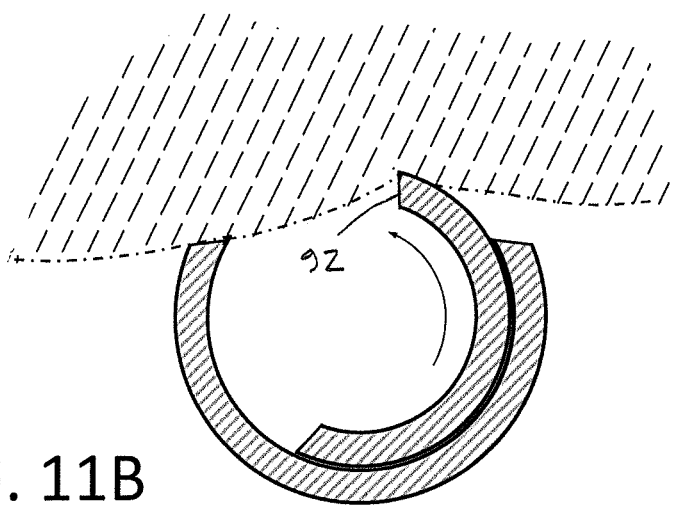

FIGS. 10A-10D provide illustrations of how the inner sleeve teeth 162 (FIG. 3) are adapted to perform two functions sequentially, wherein the needle-like tip portion 165 firstly pierces and grips tissue, and secondly the lateral cutting edges 170*a*, 170*b* function to shear off a tissue chip as such edge rotate past the cutting edges 158 of the outer sleeve 125. In FIG. 10, it can be seen that the outer sleeve 125 and its window 145 are oriented with the inner sleeve 140 and inner window 150 in a window-open position where the leading edge 160A of the inner sleeve 140 is about to contact tissue T. In this case, it can be seen that the tissue T is depicted as a hard form or tissue which is not suctioned very far through the two windows 145 150 into passageway or bore 155. As an example, such hard tissue may be a calcified fibroid in a gynecology procedure or a tendon in an arthroscopic procedure. In FIG. 10B, it can be seen that the needle-like tip 165 with vertex 180 is able to penetrate into the tissue T as the inner sleeve 140 is rotated. In FIG. 10C, it can be seen that the inner sleeve 140 is rotated further with the needle-like tip 165 still piercing and gripping tissue as the vertex 180 approaches the opposing cutting edge 158 of outer sleeve 125. FIG. 10D illustrates the pierced and gripped tissue T as it rotates further until the lateral cutting edges 170*a*, 170*b* of inner sleeve 140 have passed the cutting edge 158 of the outer sleeve 125 to shear off tissue chip TC in the extraction passageway 155 for aspiration away from the treatment site. In contrast, FIG. 11A-11B are schematic views of a typical prior art cutting assembly of the type shown in FIG. 2B wherein the rotation of the cutter does not cut hard tissue. In FIG. 11A, it can be seen that teeth and cutting edge 92, without an exceptionally sharp tip, will have the tendency to simply bump into and scrape across the surface S of hard tissue T rather than piercing into and gripping such tissue.

Figure 12A:
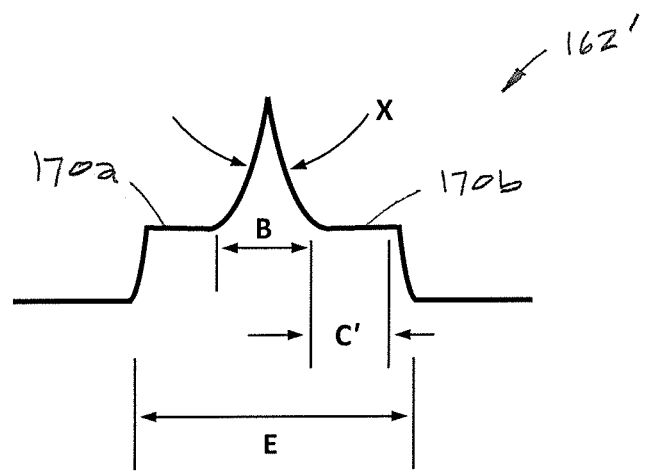
FIG. 12A is an illustration of a tooth of cutting edge similar to that of FIGS. 4 and 5 except that the of the cutting edge of the shoulder or lateral portion is elongated axially compared to the embodiment of FIG. 4.
Figure 12B:
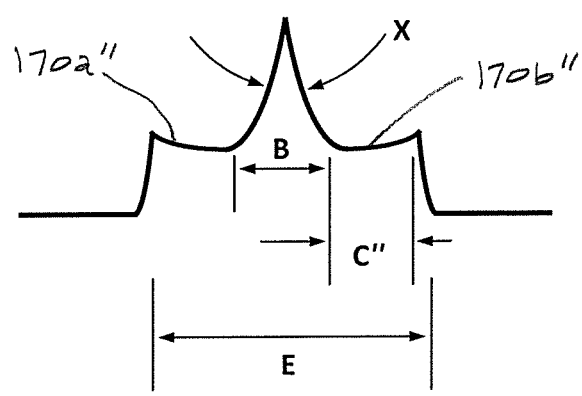
FIG. 12B is a schematic view of another tooth configuration of an inner sleeve showing a sharp needle tip with secondary edge portions that are non-linear and extend in a hook shape.

FIGS. 12A and 12B illustrate other variations of teeth 162' similar to that of FIGS. 4 through 6 where the shoulder or lateral portion 170*a*' and 170*b*' is more prominent. In FIG. 12A, it can see and be seen that the cutting edge or the lateral portion 170*a*', 170*b*' extend axially parallel to the axis of the probe 100 with more elongated cutting edges than the previous variation of FIGS. 4 and 5. In FIG. 12B, the cutting edges on the lateral portions 170*a*", 170*b*" are shown with a curvature which is also within the scope of the invention. In all other respects, the cutting edges of FIGS. 12A and 12B are similar to those of FIG. 7A-7C with respect to the sharp angles of the cutting faces relative to the outside diameter of the inner sleeve 140.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical instrument for resecting tissue, comprising:
an elongated shaft extending about a longitudinal axis, the elongated shaft comprising a co-axial outer sleeve having an outer cutting window and a coaxial inner sleeve having an inner cutting window, wherein the inner cutting window is rotatable around the longitudinal axis;
wherein the inner cutting window has circumferentially spaced-apart first and second cutting edges each with teeth therein and wherein the teeth, when viewed in a direction parallel to the longitudinal axis, define a base portion extending radially to a shoulder comprising a lateral portion and thereafter extending radially to a needle-like tip portion configured for penetrating tissue; and
wherein the teeth when viewed in cross-section from a direction transverse to the longitudinal axis define an acute angle and, wherein the needle-like tip portion is configured for piercing tissue and the lateral portion and base portion are configured to progressively engage and cut tissue after being pierced by the needle-like tip portion, wherein the needle-like tip portion comprises a point formed by arcuate sides of the lateral portion that meet at the point, wherein the arcuate sides are configured to cut tissue at an oblique angle with respect to the longitudinal axis when the inner cutting window is rotated.

2. The surgical instrument of claim 1 wherein a height of the needle-like tip portion from a tip to the lateral portion is at least 0.010".

3. The surgical instrument of claim 2 wherein a height of inner teeth from the tip to a base of the base portion is at least 0.025".

4. The surgical instrument of claim 1 wherein the lateral portion is configured with a lateral cutting edge extending at an axial direction of at least 0.005".

5. The surgical instrument of claim 4 wherein the needle-like tip portion when viewed in cross-section from a direction transverse to the longitudinal axis defines a hollow ground cutting edge.

6. The surgical instrument of claim 4 wherein the lateral cutting edge is provided on both sides of the needle-like tip portion.

7. The surgical instrument of claim 4 wherein the lateral cutting edge when viewed in cross-section from a direction transverse to the axis defines an acute angle of less than 44 degrees, less than 42 degrees, or less than 40 degrees.

8. The surgical instrument of claim 4 wherein the lateral cutting edge when viewed in cross-section from a direction transverse to the longitudinal axis defines a hollow ground cutting edge.

9. The surgical instrument of claim 4 further comprising a base cutting edge intermediate to adjacent respective lateral portions of the teeth that extends in an axial direction of at least 0.020".

10. The surgical instrument of claim 9 where the base cutting edge when viewed in cross-section from a direction transverse to the longitudinal axis defines an acute angle of less than 44 degrees, less than 42 degrees, or less than 40 degrees.

11. The surgical instrument of claim 10 wherein the base cutting edge when viewed in cross-section from a direction transverse to the longitudinal axis defines a hollow ground cutting edge.

12. The surgical instrument of claim 11 wherein the lateral cutting edge and the base cutting edge are at an outer periphery of a wall of the inner sleeve around the inner cutting window when viewed in cross-section from a direction transverse to the longitudinal axis.

13. The surgical instrument of claim 1 wherein a tip of needle-like tip portion is at an outer periphery of a wall of the inner sleeve when viewed in cross-section from a direction transverse to the longitudinal axis.

14. The surgical instrument of claim 1 wherein the outer cutting window has circumferentially spaced-apart first and second beveled cutting edges.

15. The surgical instrument of claim 14 wherein an outer cutting edge is at an inner periphery of a wall of the inner sleeve around the outer cutting window when viewed in cross-section from a direction transverse to the longitudinal axis.

16. The surgical instrument of claim 1 wherein the outer cutting window has circumferentially spaced-apart first and second cutting edges each with outer teeth therein.

17. The surgical instrument of claim 16 wherein a tip of the outer teeth is at an inner periphery of a wall of the inner sleeve around the outer cutting window when viewed in cross-section from a direction transverse to the longitudinal axis.

18. A surgical instrument for resecting tissue, comprising:
an elongate tubular cutting member extending about a longitudinal axis to a distal end having a cutting window communicating with an interior channel therein;
the cutting window having a first cutting edge and a second cutting edge circumferentially spaced-apart, wherein the first cutting edge and the second cutting edge each include a plurality of teeth therein, wherein the plurality of teeth of the first cutting edge and the second cutting edge each comprise a needle-like tip portion and a base portion, wherein the base portion extends to a shoulder comprising a lateral portion and thereafter extending radially to the needle-like tip portion configured for penetrating tissue; and
wherein the needle-like tip portion is configured for piercing tissue and the lateral portion and base portion are configured to progressively engage and cut tissue after being pierced by the needle-like tip portion, wherein the needle-like tip portion comprises a point formed by arcuate sides of the lateral portion that meet at the point, wherein the arcuate sides are configured to cut tissue at an oblique angle with respect to the longitudinal axis when the cutting window is rotated.

19. The surgical instrument of claim 18 wherein the plurality of teeth of the first cutting edge and the second cutting edge are spaced apart by a substantially linear cutting edge portion.

20. A surgical instrument for resecting tissue, comprising:
an elongate tubular cutting member extending longitudinally about a longitudinal axis to a distal end having a cutting window communicating with an interior channel therein;
the cutting window having circumferentially spaced-apart first and second cutting edges, wherein the first cutting edge and the second cutting edge each include a plurality of teeth therein;
wherein the teeth, when viewed in a direction parallel to the longitudinal axis, define a base portion extending to a shoulder comprising a lateral portion and extending thereafter to a needle-like tip portion configured for penetrating tissue;
wherein the needle-like tip portion, when viewed in cross-section from a direction transverse to the longitudinal axis, defines an acute angle of less than 44 degrees, less than 42 degrees, or less than 40 degrees; and
wherein the needle-like tip portion is configured for piercing tissue and the lateral portion and base portion are configured to progressively engage and cut tissue after being pierced by the needle-like tip portion, wherein the needle-like tip portion comprises a point formed by arcuate sides of the lateral portion that meet at the point, wherein the arcuate sides are configured to cut tissue at an oblique angle with respect to the longitudinal axis when the cutting window is rotated.

21. The surgical instrument of claim 20 wherein the plurality of teeth of the first cutting edge and the second cutting edge are spaced apart by a substantially linear cutting edge portion.

* * * * *